United States Patent
Lorenz et al.

(10) Patent No.: US 7,572,941 B2
(45) Date of Patent: Aug. 11, 2009

(54) METHOD FOR THE SEPARATION OF POLYMERIC BY-PRODUCTS FROM 1,4-BUTYNEDIOL

(75) Inventors: Rudolf Erich Lorenz, Ludwigshafen (DE); Rolf Pinkos, Bad Duerkheim (DE); Michael Steiniger, Neustadt (DE); Gerd Schaefer, Monsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/360,278

(22) Filed: Jan. 27, 2009

(65) Prior Publication Data
US 2009/0137849 A1    May 28, 2009

Related U.S. Application Data

(63) Continuation of application No. 12/065,815, filed as application No. PCT/EP2006/065595 on Aug. 23, 2006, now Pat. No. 7,524,996.

(30) Foreign Application Priority Data
Sep. 6, 2005    (DE) ............... 10 2005 042 185

(51) Int. Cl.
*C07C 29/17*    (2006.01)
(52) U.S. Cl. ............ 568/861; 568/857; 568/856
(58) Field of Classification Search .......... 568/857, 568/861, 856
See application file for complete search history.

(56) References Cited

U.S. PATENT DOCUMENTS

| | | | |
|---|---|---|---|
| 4,153,578 A | 5/1979 | De Thomas et al. |
| 4,288,640 A | 9/1981 | Schuster et al. |
| 5,068,468 A | 11/1991 | Schossig et al. |
| 5,159,092 A | 10/1992 | Leuteritz |
| 6,420,615 B1 | 7/2002 | Chaudhari et al. |

FOREIGN PATENT DOCUMENTS

| | | |
|---|---|---|
| DE | 1 941 633 | 8/1969 |
| DE | 20 40 501 | 8/1970 |
| DE | 272 644 | 10/1989 |
| DE | 42 20 239 | 12/1993 |
| EP | 0 319 208 | 11/1988 |
| EP | 0 419 419 | 9/1990 |
| EP | 1 207 146 | 5/2002 |
| GB | 13 62 071 | 7/1974 |

*Primary Examiner*—Elvis O Price
(74) *Attorney, Agent, or Firm*—Oblon, Spivak, McClelland, Maier & Neustadt, P.C.

(57) ABSTRACT

The present invention relates to processes for making 1,4-butanediol, 1,4-butenediol, or a mixture thereof by processing 1,4-butynediol in a dynamic mixing apparatus in an inert gas atmosphere at from 25 to 150° C. at a shear rate in the radial gap between rotor and stator of the mixing apparatus of more than 100 000 $\sec^{-1}$; phase separating the processed 1,4-butynediol at a temperature of from 25 to 150° C.; removing a bottom phase to obtain purified 1,4-butynediol; and reacting the purified 1,4-butynediol with hydrogen in the presence of a catalyst.

20 Claims, No Drawings

METHOD FOR THE SEPARATION OF POLYMERIC BY-PRODUCTS FROM 1,4-BUTYNEDIOL

CROSS REFERENCE TO RELATED APPLICATION

This application is a continuation of prior application Ser. No. 12/065,815, filed Mar. 5, 2008, which is a 371 of PCT/EP06/065595, filed Aug. 23, 2006, and claims priority of Germany Patent Application No. 102005042185.7, filed Sep. 6, 2005.

The invention relates to a process for purifying 1,4-butynediol by removing impurities in the form of polymeric by-products and catalyst constituents and also a process for preparing 1,4-butenediol and 1,4-butanediol by hydrogenation of the purified 1,4-butynediol, which comprises the removal of polymeric by-products.

The synthesis of 1,4-butynediol from acetylene and formaldehyde is carried out widely in industry and has been described, for example, in K. Weissermel, H.-J. Arpe, Industrielle organische Chemie, 5th edition, 1998, Wiley-VCH, pages 110 and 111. In addition to copper, the catalysts customarily used may, if appropriate, comprise bismuth and silicates (hereinafter referred to as $SiO_2$) or aluminum oxide. During the synthesis of 1,4-butynediol, the formation of oligomeric or polymeric substances (hereinafter referred to as cuprenes) occurs as secondary reaction. These cuprenes usually go together with soluble and insoluble constituents of the catalyst used into the hydrogenation stage in which 1,4-butenediol is formed first and can be hydrogenated in a further hydrogenation step to form the more important, compared to 1,4-butenediol, intermediate 1,4-butanediol.

The hydrogenation of 1,4-butynediol to 1,4-butanediol has been carried out for decades and has been described widely. Thus, U.S. Pat. No. 5,068,468 discloses the hydrogenation of 1,4-butanediol over solid supported nickel-copper catalysts, while U.S. Pat. No. 4,153,578 describes a two-stage process for hydrogenating 1,4-butynediol over suspended Raney nickel-molybdenum catalysts at a pressure of 21 bar. DD-A 272 644 discloses the suspension hydrogenation of aqueous butynediol over nickel-$SiO_2$ catalysts and general hydrogenation processes which can be applied, inter alia, to 1,4-butynediol are known from EP-B 0 319 208, DE-A 19 41 633 and DE-A 20 40 501.

Cuprenes and catalyst constituents from the butynediol synthesis interfere in its hydrogenation to 1,4-butenediol or 1,4-butanediol and significantly impair the hydrogenation result. Thus, cuprenes deposit on the catalyst and hinder contact of butynediol with the catalyst surface, as a result of which the reaction becomes slower. Catalyst components such as copper, bismuth and/or $SiO_2$ likewise deposit on the catalyst and thus change the catalyst activity and selectivity.

Even without removal of the catalyst from the reactor, these disadvantageous effects can be followed by monitoring the formation of the by-product butanol, since its formation is accelerated by the abovementioned catalyst poisons.

The simple purification of 1,4-butynediol, e.g. by filtration, is not readily possible since the cuprenes and $SiO_2$, in particular, are partly present in colloidal or very finely dispersed form and thus quickly block convent onal filters, so that the filters either have to be continually replaced or be backflushed in a complicated procedure.

It is an object of the invention to provide a simple economical process by means of which the components which are undesirable in the hydrogenation stage can be removed from 1,4-butynediol to give a purified 1,4-butynediol from which 1,4-butenediol or 1,4-butanediol can be obtained with high selectivity and with a good catalyst operating life by hydrogenation.

It has now surprisingly been found that a process which comprises processing technical-grade 1,4-butynediol in a dynamic mixing apparatus in an inert gas atmosphere at from 25 to 150° C., preferably from 70 to 90° C., at a shear rate in the radial gap between rotor and stator of the mixing apparatus of more than 100 000 $sec^{-1}$, awaiting phase separation at temperatures of from 25 to 150° C. and separating off the bottom phase leads to removal of the components which are undesirable in the hydrogenation stage from technical-grade 1,4-butynediol and makes it possible to obtain 1,4-butenediol and 1,4-butanediol by hydrogenation, each with high selectivity and with a good catalyst operating life. In the present patent application, technical-grade 1,4-butynediol is 1,4-butynediol which has been prepared from acetylene and formaldehyde over customary catalysts known per se and has not been purified, for example by distillation, after its synthesis and generally comprises from 10 to 70% by weight of butynediol, preferably from 30 to 60% by weight of butynediol, from 0.2 to 4% by weight of propynol, from 0.1-2% by weight of formaldehyde and from 1 to 2000 ppm, preferably from 3 to 500 ppm, particularly preferably from 10 to 200 ppm, of cuprenes and catalyst constituents and also <0.1% of other impurities.

1,4-Butynediol is preferably processed at a shear rate of from 130 000 to 145 000 $sec^{-1}$ for from 5 minutes to 1 hour, preferably from 10 minutes to 20 minutes.

The treatment of the 1,4-butynediol at the shear rate according to the invention can be effected in commercial mixing apparatuses, in particular dynamic mixing apparatuses, which are suitable for setting such shear rates and for producing a liquid mixture, which may optionally comprise gaseous constituents, of at least two, in particular chemically reactive, components and which have a regulating facility for setting the temperature. In the process of the invention, the butynediol is heated to from 25 to 150° C., preferably from 70 to 90° C., before the mixing chamber. However, mixing apparatuses which ensure a shear rate in the radial gap between rotor and wall of the housing of more than 100 000 ($10^5$) $sec^{-1}$ are preferred. Such a mixing apparatus or mixing chamber is known from, for example, DE-C 42 20 239. This mixing chamber is a mixing apparatus for producing a liquid mixture, which may optionally comprise gaseous constituents, which mixing apparatus has a rotationally symmetric mixing chamber which is formed by a circumferential wall and two end faces and has at least one outlet opening for the mixture in the circumference wall of the mixing chamber and has a rotor which is located in the mixing chamber and can be driven so that it rotates, with the rotor having edge notches uniformly distributed around its circumference and recesses at its end faces which together with annular channels in the end faces of the mixing chamber form pressure cells which are connected to one another via through-holes in the rotor. The disclosure of this DE-C 42 20 239 is fully incorporated by reference. A shear rate of more than 100 000 ($10^5$) $sec^{-1}$ can be achieved in this mixing chamber by means of a suitable design of the rotor in relation to the inner wall of the housing.

The inert gas is introduced preferably directly via a connection into the mixing chamber at a pressure of generally from 1 to 2 bar and is selected from among nitrogen, carbon dioxide, helium, neon, argon, krypton and xenon and mixtures thereof.

At the temperature at which shear occurs according to the invention, phase separation is then awaited in a calming zone in which mixing no longer occurs. This can be effected in one or more separate phase separation vessels which should be designed so that the temperature can be regulated. The time to occurrence of phase separation is generally from one hour (h) to 5 hours, preferably from 2 hours to 5 hours.

During storage in the calming zone, two phases are formed and these are then separated from one another using methods known per se for this purpose, e.g. by decantation or centrifugation, preferably by centrifugation using commercial centrifuges.

The heavier (bottom) phase comprises predominantly the cuprenes and also considerable amounts of copper-, bismuth- or $SiO_2$-comprising, undesirable catalyst components. This bottom phase is either passed to disposal, e.g. incineration, or can be treated beforehand, e.g. by distillation, to separate off residual 1,4-butynediol which can be recirculated to the process of the invention. The upper phase which has been largely freed of cuprenes and undesirable catalyst constituents is passed to the hydrogenation to form 1,4-butenediol or 1,4-butanediol.

The purification process of the invention can be carried out batchwise or fully continuously, with a continuous process being preferred.

In addition, the present invention provides a process for the hydrogenation of 1,4-butynediol to 1,4-butenediol and preferably to 1,4-butanediol, in which 1,4-butynediol which has been purified by the process of the invention is used.

The hydrogenation of 1,4-butynediol is known per se and is preferably carried out in the liquid phase over fixed-bed and/or suspended catalysts. The hydrogenation can be carried out to the stage of 1,4-butanediol but also only to the stage of 1,4-butenediol.

The hydrogenation of purified 1,4-butynediol is carried out using catalysts which are able to hydrogenate C-C triple and double bonds to single bonds. They generally comprise one or more elements of transition group I, VI, VII or VIII of the Periodic Table of the Elements, preferably the elements copper, chromium, molybdenum, manganese, rhenium, iron, ruthenium, cobalt, nickel, platinum and palladium. Particular preference is given to using catalysts which comprise at least one element selected from among copper, chromium, molybdenum, iron, nickel, platinum and palladium.

The metal content of these catalysts is generally 0.1-100% by weight, preferably 0.2-95% by weight, particularly preferably 0.5-95% by weight.

The catalyst preferably further comprises at least one element selected from among the elements of main groups II, III, IV and VI, transition groups II, III, IV and V of the Periodic Table of the Elements and the lanthanides as promoter to increase the activity.

The promoter content of the catalyst is generally up to 5% by weight, preferably 0.001-5% by weight, particularly preferably 0.01-3% by weight.

As catalysts, it is possible to use precipitated catalysts, supported catalysts or Raney-type catalysts whose preparation is described, for example, in Ullmanns Encyclopädie der technischen Chemie, 4th edition, 1977, volume 13, pages 558-665.

As support materials, it is possible to use aluminum oxides, titanium oxides, zirconium dioxide, silicon dioxide, clay minerals, e.g. montmorillonites, silicates such as magnesium silicates or aluminum silicates, zeolites and activated carbon. Preferred support materials are aluminum oxides, titanium dioxides, silicon dioxide, zirconium dioxide and activated carbon. Of course, it is also possible for mixtures of various support materials to serve as support for catalysts which can be employed in the process of the invention.

These catalysts can be used either as shaped catalyst bodies, for example as spheres, cylinders, rings, spirals, or in the form of powders.

Suitable Raney-type catalysts are, for example: Raney nickel, Raney copper, Raney cobalt, Raney nickel/molybdenum, Raney nickel/copper, Raney nickel/chromium, Raney nickel/chromium/iron or rhenium sponge. Raney nickel/molybdenum catalysts can be prepared, for example, by the process described in U.S. Pat. No. 4,153,578. However, these catalysts are also marketed by, for example, Degussa, 63403 Hanau, Germany. A Raney nickel-chromium-iron catalyst is marketed, for example, by Degussa under the trade name catalyst type 11 112 W®.

When precipitated or supported catalysts are used, these are reduced at from 150 to 500° C. in a stream of hydrogen or hydrogen/inert gas at the beginning of the reaction. This reduction can be carried out directly in the synthesis reactor. If the reduction is carried out in a separate reactor, the surface of the catalysts can be passivated by means of oxygen-comprising gas mixtures at 30° C. before removal from the reactor. The passivated catalysts can in this case be activated at 180° C. in a stream of nitrogen/hydrogen in the synthesis reactor prior to use or can be used without activation.

The catalysts can be used in a fixed bed or in suspension. If the catalysts are present in the form of a fixed bed, the reactor is not operated in the usual downflow mode but instead with an upward-directed cocurrent of liquid and gas so that the liquid and not the gas is present as continuous phase.

When suspended catalysts are used, they generally have a particle size of 0.1-500 µm, preferably from 0.5 to 200 µm, particularly preferably from 1 to 100 µm.

If the process is carried out using suspended catalysts and packed bubble columns, an upward-directed cocurrent of liquid and gas in which the liquid and not the gas is present as continuous phase is likewise employed. The ratio of amount of gas leaving the reaction vessel and amount of gas fed in is, both when using fixed-bed reactors and when using packed bubble columns and a catalyst suspended in the reaction medium, from 0.99:1 to 0.4:1.

The ratio of amount of gas leaving the reaction vessel and amount of gas fed in which is to be adhered to according to the invention in the case of fixed-bed reactors and in the case of catalysts suspended in the reaction medium in packed bubble columns can be set in a simple manner either by metering in the appropriate amount of hydrogen as fresh gas or, preferably, recirculating recycle gas and replacing only the hydrogen lost by chemical consumption and in the offgas by fresh hydrogen.

The molar ratio of hydrogen to 1,4-butynediol in the reactor is at least 3:1, preferably from 4:1 to 100:1.

The process of the invention is carried out over fixed-bed catalysts in the gas recycle mode, i.e. the gas leaving the reactor is recirculated, if appropriate after being supplemented with fresh hydrogen, via a compressor to the reactor. It is possible for the total amount of recycle gas or part thereof to be circulated via a jet compressor. In this preferred embodiment, the recycled gas compressor is replaced by an inexpensive nozzle. The work of compression is introduced via the liquid which is likewise circulated. The increase in the pressure of the liquid required for operating the jet compressor is about 3-5 bar.

Suitable reactors for carrying out the process of the invention using a catalyst suspended in the reaction medium are jet nozzle reactors, stirred tanks and bubble columns with packing having a packing surface area of at least 500 $m^2/m^3$, preferably from 1000 $m^2/m^3$ to 2000 $m^2/m^3$. Various types of jet nozzle reactors can be employed as long as they have a sufficiently high energy input, on the basis of experience above 2 kW/m³, to ensure the high mass transfer from the gas phase to the liquid with the suspended catalyst particles which is essential for the invention. Jet nozzle reactors equipped with a momentum exchange tube are particularly useful. A type of jet nozzle reactor which is widespread in industry is, for example, the reactor described in EP-A 0 419 419. At energy inputs of from 3 to 5 kW/m³, separation of the gas phase in simple separators is still possible without having to use additional apparatuses such as foam centrifuges or cyclones when this reactor is employed.

Stirred tanks are suitable for carrying out the process of the invention only when the energy input is in the range from 2 to 10 kW/m³.

Jet nozzle reactors with suspended catalysts require energy inputs per unit volume of more than 2 kW/m³, preferably 3-5 kW/m³.

1,4-Butanediol is employed in large quantities in industry, for example in the production of THF or as diol component in polyesters.

EXAMPLES

The process of the invention is illustrated by the following examples. Unless indicated otherwise, technical-grade 1,4-butynediol in the form of a 54% strength by weight aqueous solution was used. The percentages reported for the reaction product mixtures in the examples are, unless indicated otherwise, percentages by weight calculated on a water-free basis and determined by gas chromatography.

Comparative Example

Technical-Grade 1,4-butynediol 190 ml of an Ni catalyst as described in example 1 of U.S. Pat. No. 5,068,468 were introduced into a hydrogenation reactor having a length of 1.2 m. Technical-grade 1,4-butynediol in the form of a 54% strength by weight aqueous solution was fed into the reactor at a feed rate of 100 g/h. Hydrogenation was carried out for 2 weeks at a temperature of 140° C., a hydrogen pressure of 200 bar and a liquid circulation of 800 ml/h.

Within the time of the experiment (2 weeks), the butynediol conversion was always quantitative. The average increase in n-butanol was about 0.06% per day. After the catalyst was removed from the reactor, solid deposits were present on the catalyst. The yield of 1,4-butanediol, based on butynediol used, was 98.3% by weight at the beginning but was reduced by 0.06% by weight each day.

Example 1

Purification of 1,4-butynediol

Purification:

Technical-grade butynediol in the form of a 54% strength by weight aqueous solution was sheared by means of a mixing apparatus as described in FIG. 1 of DE-C 42 20 239 having a gap width of 0.05 mm and a rotor diameter of 48 mm at 80° C. for 10 minutes and was subsequently calmed at 80° C. for 22 hours until phase separation occurred. It was then cooled to 25° C. and the bottom phase was separated off by decantation. The butynediol which had been purified in this way was fed to the hydrogenation reactor.

Hydrogenation:

The hydrogenation was carried out in a manner analogous to the comparative example using the 1,4-butynediol which had been prepurified according to the invention. The average increase in n-butanol was only about 0.035% per day. After removal of the catalyst from the reactor, no deposits were found. The yield of 1,4-butanediol, based on butynediol used, was 98.3% by weight at the beginning and was reduced by 0.035% by weight each day.

The invention claimed is:

1. A process for making 1,4-butanediol, 1,4-butenediol, or a mixture thereof, comprising:
   processing 1,4-butynediol in a dynamic mixing apparatus in an inert gas atmosphere at from 25 to 150° C. at a shear rate in the radial gap between rotor and stator of the mixing apparatus of more than 100 000 sec$^{-1}$;
   phase separating the processed 1,4-butynediol at a temperature of from 25 to 150° C.;
   removing a bottom phase to obtain purified 1,4-butynediol; and
   reacting said purified 1,4-butynediol with hydrogen in the presence of a catalyst.

2. The process according to claim 1 for preparing 1,4-butenediol.

3. The process according to claim 1 for preparing 1,4-butanediol.

4. The process according to claim 1, wherein said catalyst comprises at least one metal selected from the group consisting of copper, chromium, molybdenum, manganese, rhenium, iron, ruthenium, cobalt, nickel, platinum, and palladium.

5. The process according to claim 4, wherein said catalyst comprises at least one metal element selected from the group consisting of copper, chromium, iron, nickel, platinum, and palladium.

6. The process according to claim 4, wherein said at least one metal is present in an amount ranging from 0.1-100% by weight of said catalyst.

7. The process according to claim 4, wherein said at least one metal is present in an amount ranging from 0.2-95% by weight of said catalyst.

8. The process according to claim 4, wherein said at least one metal is present in an amount ranging from 0.5-95% by weight of said catalyst.

9. The process according to claim 4, wherein said catalyst further comprises at least one promoter selected from the group consisting of a main group II element, a main group III element, a main group IV element, a main group VI element, a transition group II element, a transition group III element, a transition group IV element, a transition group V element, and a lanthanide.

10. The process according to claim 9, wherein said at least one promoter is present in an amount of at most 5% by weight of said catalyst.

11. The process according to claim 9, wherein said at least one promoter is present in an amount ranging from 0.001-5% by weight of said catalyst.

12. The process according to claim 9, wherein said at least one promoter is present in an amount ranging from 0.01-3% by weight of said catalyst.

13. The process according to claim 1, wherein a molar ratio of hydrogen to purified 1,4-butynediol is at least 3:1.

14. The process according to claim 1, wherein a molar ratio of hydrogen to purified 1,4-butynediol is from 4:1 to 100:1.

15. The process according to claim 1, wherein said catalyst is in the form of a fixed-bed, a suspension, or a combination thereof.

16. The process according to claim 15, wherein said catalyst in the form of a fixed-bed exhibits a particle size of 0.1 to 500 µm.

17. The process according to claim 1, wherein said catalyst is in the form of a precipitated catalyst, a supported catalyst, or a Raney catalyst.

18. The process according to claim 1, wherein said catalyst is in the form of a support catalyst and comprises at least one support selected from the group consisting of an aluminum oxide, a titanium oxide, zirconium dioxide, silicon dioxide, a montmorillonite, a magnesium silicate, an aluminum silicate, a zeolite, and activated carbon.

19. The process according to claim 1, wherein said shear rate is from 130,000 to 145,000 $sec^{-1}$.

20. The process according to claim 1, wherein said processing occurs for 5 minutes to 1 hour.

* * * * *